(12) United States Patent
Grevin (10) Patent No.: US 8,444,610 B2
(45) Date of Patent: May 21, 2013

(54) ASSEMBLY FOR CONDITIONING AND DISPENSING A MEDICAL LIQUID

(75) Inventor: Guillaume Grevin, L'Isle d'Abeau (FR)

(73) Assignee: Rexam Pharma, Offranville (FR)

( * ) Notice: Subject to any disclaimer, the term of this patent is extended or adjusted under 35 U.S.C. 154(b) by 652 days.

(21) Appl. No.: 12/522,793

(22) PCT Filed: Jan. 3, 2008

(86) PCT No.: PCT/FR2008/000010
§ 371 (c)(1),
(2), (4) Date: Jan. 29, 2010

(87) PCT Pub. No.: WO2008/099079
PCT Pub. Date: Aug. 21, 2008

(65) Prior Publication Data
US 2010/0145287 A1    Jun. 10, 2010

(30) Foreign Application Priority Data

Jan. 12, 2007 (FR) ...................... 07 00245

(51) Int. Cl.
*A61M 35/00* (2006.01)
*B65D 47/18* (2006.01)
(52) U.S. Cl.
CPC ............... *A61M 35/00* (2013.01); *B65D 47/18* (2013.01)
USPC .......................................... 604/298; 222/420
(58) Field of Classification Search
USPC ...................................................... 215/219
See application file for complete search history.

(56) References Cited

U.S. PATENT DOCUMENTS

| 3,399,796 | A | * | 9/1968 | Steiner | 215/216 |
| 3,667,636 | A | * | 6/1972 | Landen | 215/214 |
| 3,837,518 | A | * | 9/1974 | Gach | 215/365 |
| 3,881,624 | A | * | 5/1975 | Dougherty, Sr. | 215/221 |
| 3,917,097 | A | * | 11/1975 | Uhlig | 215/216 |
| 3,974,929 | A | * | 8/1976 | Montgomery | 215/216 |
| 4,002,275 | A | * | 1/1977 | Crowle et al. | 222/543 |
| 4,330,067 | A | * | 5/1982 | Deussen | 215/220 |
| 4,351,442 | A | * | 9/1982 | Summers | 215/216 |
| 4,522,307 | A | * | 6/1985 | Steiner | 215/219 |

(Continued)

FOREIGN PATENT DOCUMENTS

| DE | 93 12 423 | 2/1994 |
| EP | 0 111 419 | 6/1984 |

(Continued)

OTHER PUBLICATIONS

International Search Report dated Aug. 29, 2008, from corresponding PCT application.

*Primary Examiner* — Melanie Hand
*Assistant Examiner* — Paula Craig
(74) *Attorney, Agent, or Firm* — Young & Thompson (57) ABSTRACT

This assembly is of the type including: a vessel (4) for containing liquid, the vessel (4) having a neck (14); a dispensing dropper end fitting (6) disposed at the end of the neck (14); and a cap (8) for closing the vessel (4), provided to be screwed onto the neck (14). In a preferred embodiment, the cap (8) and the neck (14) have safety element preventing the cap (8) from being unscrewed simply by applying an unscrewing torque, and allowing the cap (8) to be unscrewed when an additional action is applied together with the torque for unscrewing the cap (8).

24 Claims, 4 Drawing Sheets

U.S. PATENT DOCUMENTS

| | | | | |
|---|---|---|---|---|
| 4,529,096 A | * | 7/1985 | Chartier et al. | 215/252 |
| 4,548,329 A | * | 10/1985 | Curry | 215/216 |
| 4,551,371 A | * | 11/1985 | Eckstein | 222/92 |
| 4,588,097 A | * | 5/1986 | Hauser | 215/216 |
| 4,667,836 A | * | 5/1987 | McLaren | 215/216 |
| 4,709,824 A | * | 12/1987 | Thompson | 215/252 |
| 5,246,145 A | * | 9/1993 | Leoncavallo et al. | 222/153.14 |
| 5,328,058 A | * | 7/1994 | Leoncavallo et al. | 222/153.14 |
| 5,624,057 A | * | 4/1997 | Lifshey | 222/212 |
| 5,673,808 A | * | 10/1997 | Valyi et al. | 215/252 |
| 5,687,863 A | * | 11/1997 | Kusz | 215/216 |
| 5,915,576 A | * | 6/1999 | Robinson | 215/216 |
| 5,918,752 A | * | 7/1999 | Meyer | 215/204 |
| 5,927,527 A | * | 7/1999 | Montgomery et al. | 215/219 |
| 5,975,381 A | * | 11/1999 | Revenu | 222/563 |
| 6,000,578 A | * | 12/1999 | Boissay | 222/83 |
| 6,102,223 A | * | 8/2000 | Montgomery | 215/216 |
| 6,161,711 A | * | 12/2000 | Miceli et al. | 215/206 |
| 6,334,557 B1 | * | 1/2002 | Yang | 222/567 |
| 6,398,766 B1 | * | 6/2002 | Branch | 604/302 |
| 6,561,370 B1 | * | 5/2003 | Escobar-Harrity | 215/218 |
| 6,612,469 B2 | * | 9/2003 | Lopez Pardo | 222/214 |
| 6,854,613 B2 | * | 2/2005 | Biesecker et al. | 215/219 |
| 7,488,303 B1 | * | 2/2009 | Haffner et al. | 604/8 |
| 7,628,283 B2 | * | 12/2009 | Shingle | 215/209 |
| 2003/0039781 A1 | * | 2/2003 | D'Alessio et al. | 428/35.7 |
| 2003/0181354 A1 | * | 9/2003 | Abdulrazik | 514/1 |
| 2003/0222046 A1 | * | 12/2003 | Schenck et al. | 215/341 |
| 2004/0079671 A1 | * | 4/2004 | Bandyopadhyay et al. | 206/528 |
| 2004/0140319 A1 | * | 7/2004 | Gerondale | 222/1 |
| 2004/0182814 A1 | * | 9/2004 | Suffa | 215/216 |
| 2005/0267423 A1 | * | 12/2005 | Johnson et al. | 604/295 |
| 2006/0111680 A1 | | 5/2006 | Spada et al. | |
| 2007/0233021 A1 | * | 10/2007 | Poisson et al. | 604/295 |
| 2009/0192266 A1 | * | 7/2009 | Talkowski et al. | 525/170 |

FOREIGN PATENT DOCUMENTS

| | | |
|---|---|---|
| EP | 0 343 778 | 11/1989 |
| FR | 2 414 005 | 8/1979 |
| GB | 2 256 638 | 12/1992 |

* cited by examiner

ASSEMBLY FOR CONDITIONING AND DISPENSING A MEDICAL LIQUID

This application is a national phase application of PCT/FR2008/000010 filed Jan. 3, 2008, which claims priority to French application No. 0700245 filed Jan. 12, 2007.

The present invention relates to an assembly for holding and dispensing a medical liquid, of the type comprising:
- a vessel for containing liquid, the vessel having a neck;
- a dispensing dropper end fitting disposed at the end of the neck, the end fitting and the vessel allowing liquid to be dispensed drop by drop by squeezing the vessel between the fingers of one hand; and
- an end cap for the vessel, provided to be screwed onto the neck.

SUMMARY OF THE INVENTION

In a holding and dispensing assembly of this type, the risks of a child using the liquid inappropriately without being monitored by an adult, for example by ingesting it, are very limited because of the presence of the dropper end fitting, which limits the amounts of liquid dispensed. Furthermore, ophthalmic medical liquids such as collyria, to be dispensed onto the eye, are generally not considered very dangerous.

Nevertheless, it is desirable to limit the risks of inappropriate use.

One object of the invention is to provide an assembly for holding and dispensing an ophthalmic medical liquid which makes it possible to limit the risks of inappropriate use, in particular by a child.

For this purpose, the invention proposes an assembly for holding and dispensing a medical liquid of the aforementioned type, characterized in that the cap and the neck have safety means preventing the cap from being unscrewed only by applying an unscrewing torque, and allowing the cap to be unscrewed when an additional action is applied together with the torque for unscrewing the cap.

In other embodiments, the holding and dispensing assembly comprises one or more of the following features, taken individually or in any technically feasible combination:
- the vessel is made of a material or mixture of materials having a Young's modulus less than the Young's modulus of the material or mixture of materials of which the cap is made;
- the vessel and the cap are each made from a material or mixture of materials selected from the following materials: low-density polyethylene (LDPE), medium-density polyethylene (MDPE), high-density polyethylene (HDPE), polypropylene and polyethylene terephthalate (PET);
- the vessel and the cap are made from low-density polyethylene (LDPE) and high-density polyethylene (HDPE), the cap having a greater proportion by mass of high-density polyethylene (HDPE) than the vessel;
- the vessel consists purely of low-density polyethylene (LDPE), and the cap comprises at least 20% by mass of high-density polyethylene (HDPE), the remainder consisting of low-density polyethylene (LDPE);
- the vessel has a capacity of less than 30 ml, preferably less than 20 ml;
- the safety means make it possible to unscrew the cap if the cap is squeezed during the unscrewing;
- the safety means have means for the unidirectional blocking of the rotation of the cap relative to the neck, wherein it is possible to disengage the unidirectional blocking means by squeezing the cap;
- the cap has a first external skirt, coaxial with and enclosing a second skirt bearing a thread for screwing the cap onto the neck, the blocking means having at least one internal feature on the first skirt and at least one external feature on the neck, which features are complementary and can be disengaged from one another by squeezing the first skirt in two regions which are angularly offset relative to the or to each internal feature;
- the blocking means have two diametrically opposite internal features, disposed on the skirt and angularly offset by 90° relative to the pressing regions, the neck comprising two diametrically opposite external features;
- the or each external feature of the neck is formed by a lug projecting radially towards the outside of the neck, the lug having a radial blocking surface, a sliding surface inclined as a whole relative to the blocking surface, and a transition surface extending between the blocking surface and the sliding surface, the transition surface being substantially perpendicular to the blocking surface;
- the neck has an annular reinforcing rim extending so as to project towards the outside of the neck and passing through the external features so as to rigidify them;
- it comprises a first-opening indicator in the form of a tamper-evident band connected to the cap by a brittle region which breaks when the cap is first opened;
- the cap has an element for closing the end fitting tightly, sealing the end fitting at least over the part of the path of the cap during which the safety means operate to ensure the tightness and the sterility of the inside of the vessel;
- the vessel contains an ophthalmic medical liquid of the collyrium type.

BRIEF DESCRIPTION OF THE DRAWINGS

The invention and its benefits will be better understood upon reading the following description, given purely by way of example and in reference to the appended drawings, in which.

DETAILED DESCRIPTION OF THE PREFERRED EMBODIMENTS

Figure 1:
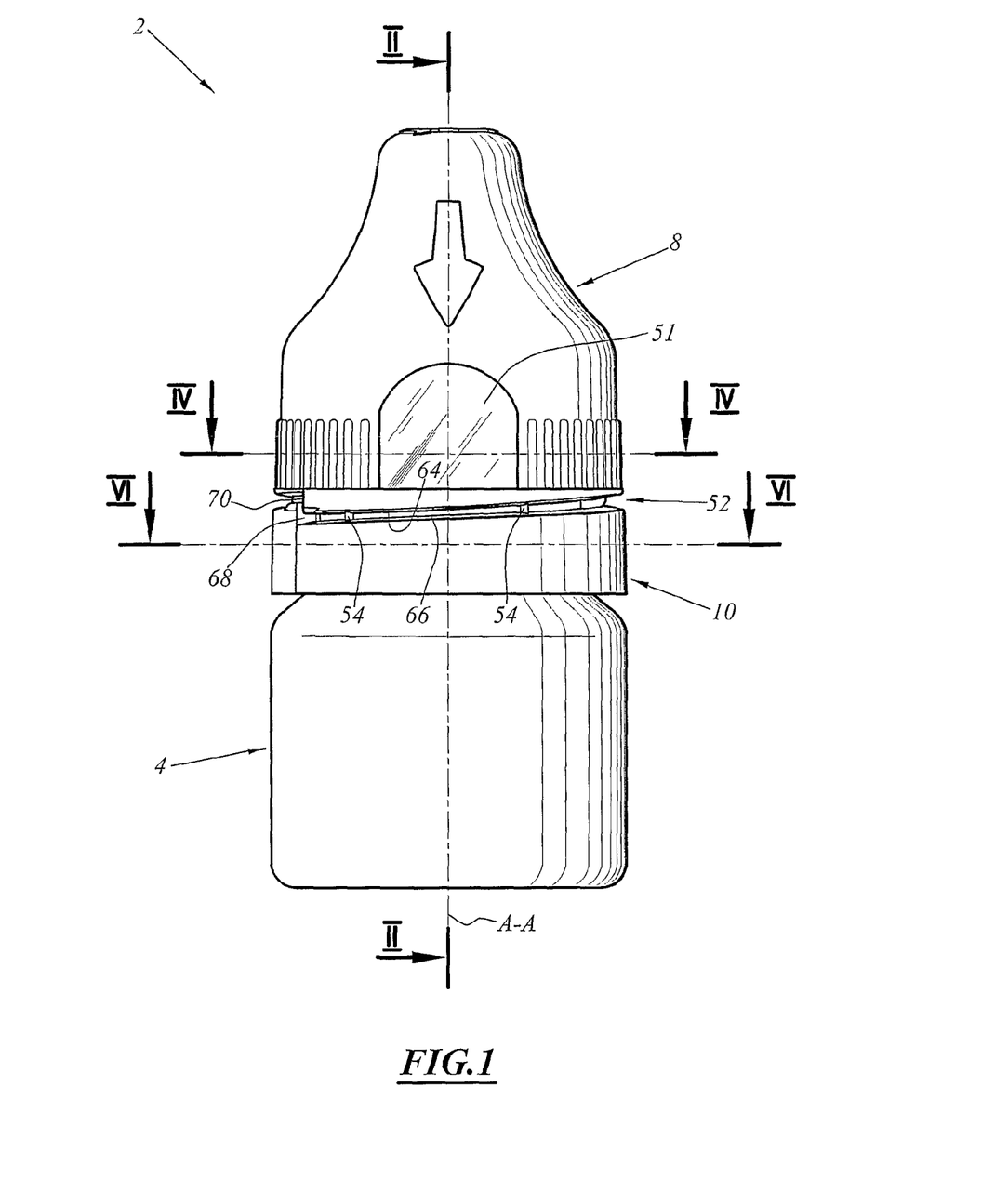
FIG. 1 is a side elevation of a holding and dispensing assembly according to the invention.
Figure 2:
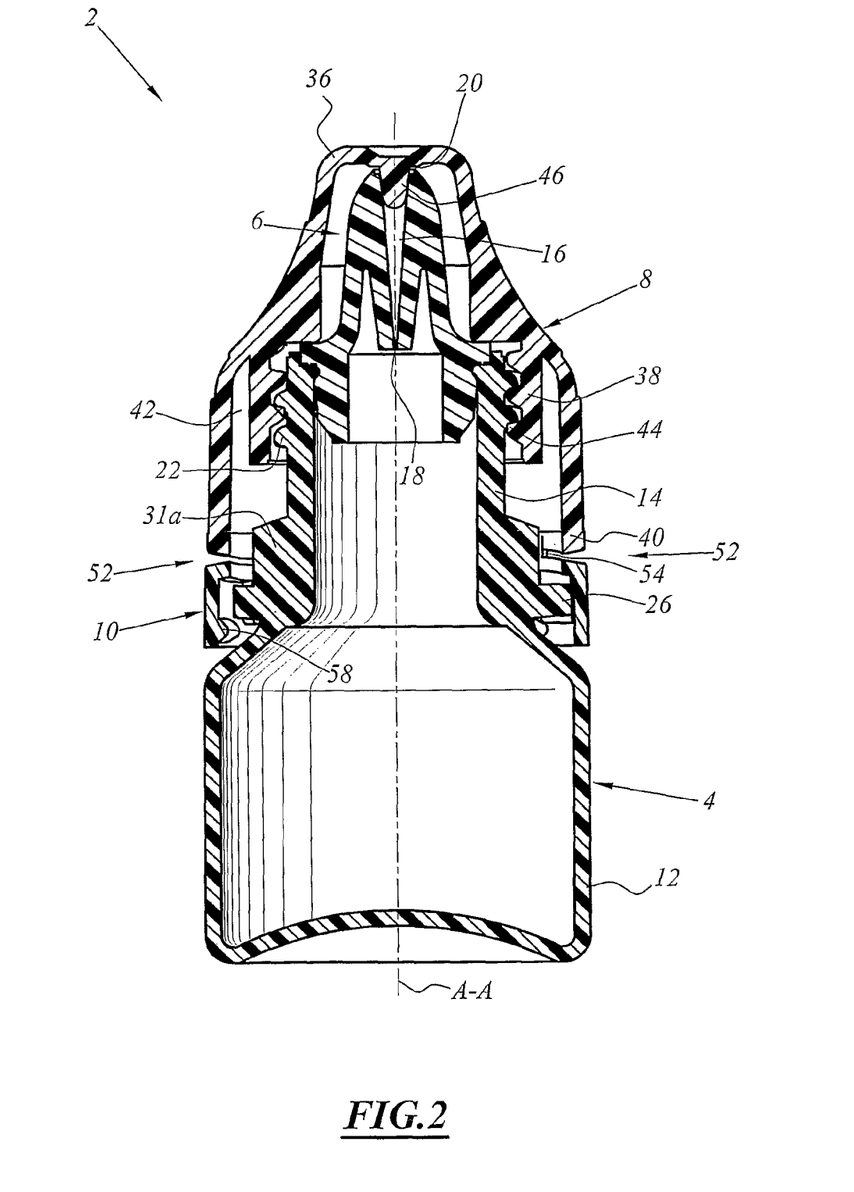
FIG. 2 is a sectional view along II-II of the assembly of FIG. 1.
Figure 3:
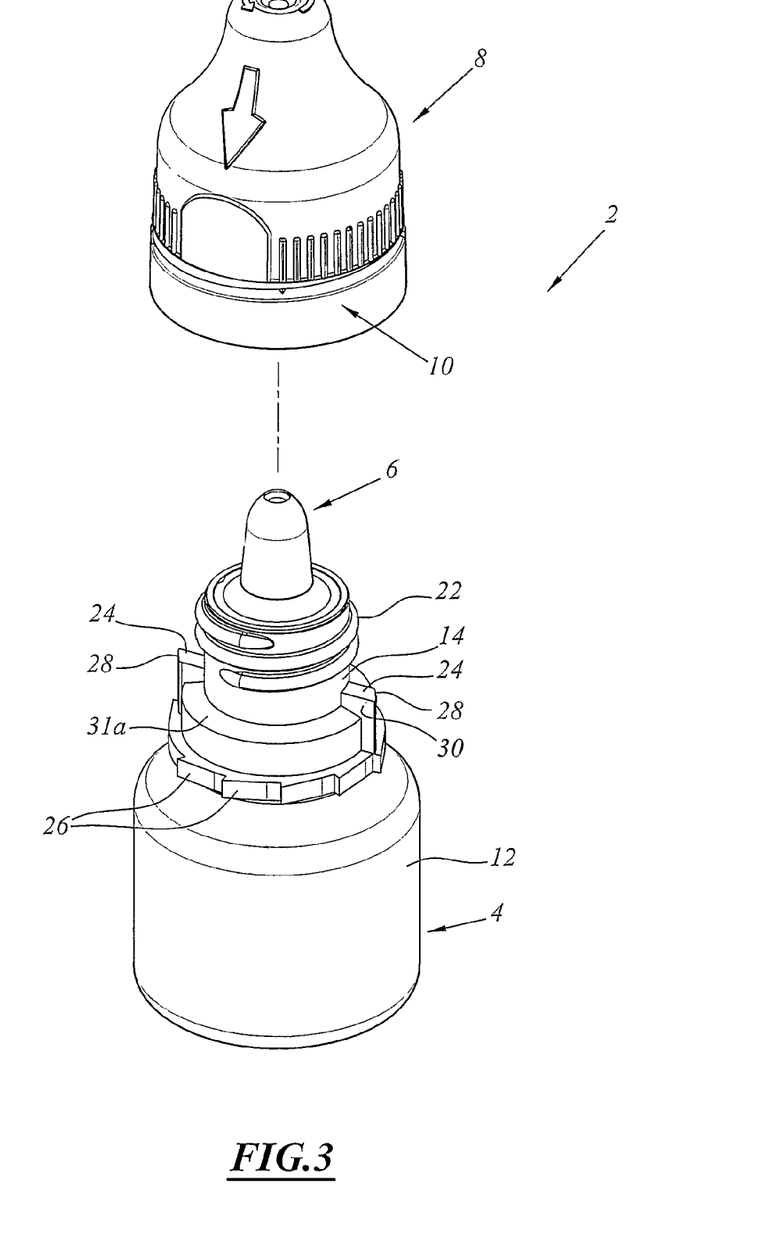
FIG. 3 is a perspective view of the holding and dispensing assembly of FIG. 1, before mounting a cap for the assembly.

FIGS. 1 to 3 show an assembly 2 for holding and dispensing a collyrium in the form of an aqueous solution.

The assembly 2 comprises a vessel 4 for containing the collyrium, a dropper end fitting 6 (FIGS. 2 and 3), a cap 8 for closing the vessel 4, and a tamper-evident band or ring 10 forming the first-opening indicator of the assembly 2.

In the example shown, the vessel 4 is a plastics material flask containing the collyrium, which has not been shown in the figures.

As shown in FIGS. 2 and 3, the vessel 4 has a hollow body 12 prolonged by a neck 14 which extends along a longitudinal axis A-A.

The walls of the body 12 can be elastically deformed by squeezing to cause a reduction in the internal volume of the body 12 and the expulsion of the collyrium through the neck 14.

As shown in FIGS. 2 and 3, the end fitting 6 is plugged into the neck 14. The end fitting 6 has a duct 16 for the collyrium to pass through, widening progressively between an upstream opening 18 (at the bottom in FIG. 2) and a downstream opening 20.

The duct 16 makes it possible to dispense the collyrium drop by drop, with a calibrated drop size, when the user squeezes the body 12 between his fingers.

The neck 14 has a plurality of external features comprising, from the outside of the neck 14 opposite the body 12 towards said body, an upper thread 22, intermediate lugs 24 (FIG. 3), and lower teeth 26.

Figure 4:
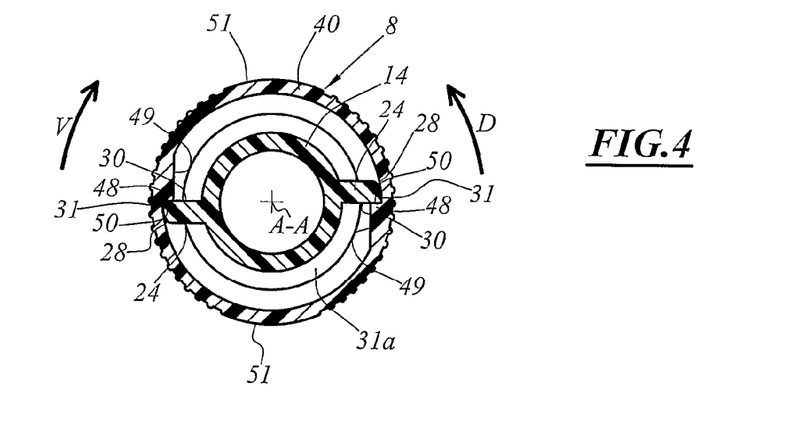
FIG. 4 is a sectional view along IV-IV of FIG. 1, showing the cap in a resting configuration.
Figure 5:
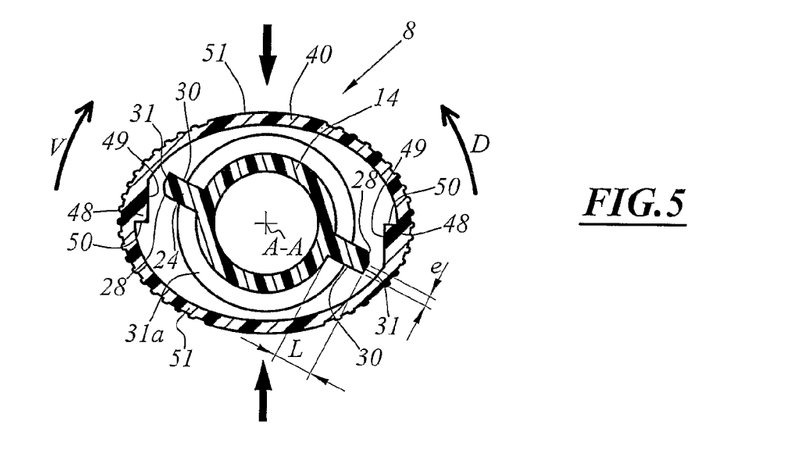
FIG. 5 is a view analogous to that of FIG. 4, showing the cap in a configuration deformed by squeezing.

As shown in FIGS. 3 to 5, the neck 14 comprises two diametrically opposed lugs 24 projecting radially towards the outside of the neck 14.

Each lug 24 extends radially towards the outside from the neck 14, and has at the external end thereof a sliding surface 28 and a substantially radial blocking surface 30.

Each lug 24 has a transition surface 31 (FIGS. 4 and 5) extending between the sliding surface 28 and the blocking surface 30. The transition surface 31 is substantially perpendicular to the blocking surface 30. The transition surface ensures that the lug 24 has a minimum thickness at the outer end thereof to ensure sufficient rigidity of the lug 24.

The neck 14 has an annular reinforcing ring 31a extending so as to project radially towards the outside from the neck 14, at the height of the lugs 24.

In this way, the rim 31a provides each lug 24 with flexural rigidity in the circumferential direction.

The height of the rim 31a, along the axis A-A, is less than that of the lugs 24.

The rim 31a has an external diameter which is less than the diameter of the imaginary circle passing through the outer ends of the lugs 24, so as not to prevent said outer ends from engaging with the complementary features of the cap 8, as will be described in the following.

It will be noted that the lugs 24 are not visible in FIG. 2 because the sectional plane does not pass through the lugs 24. The sectional plane of FIG. 3 passes above the rim 31a.

Figure 6:
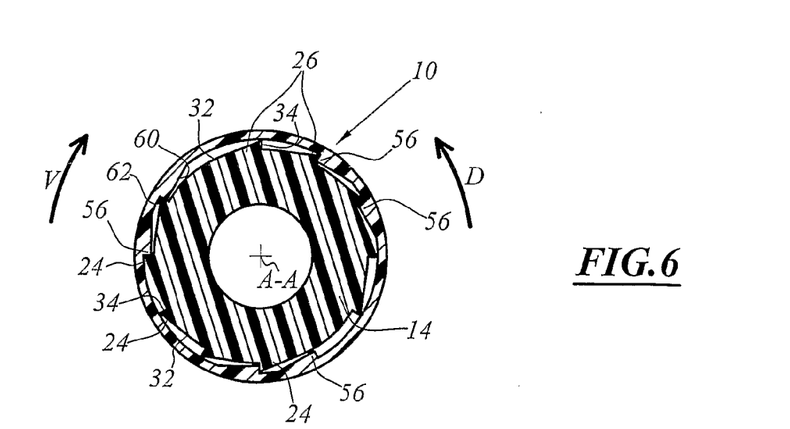
FIG. 6 is a sectional view along VI-VI of FIG. 1.

As shown in FIG. 6, the neck 14 has a plurality of teeth 26 distributed around the neck 14 and projecting towards the outside. In this case, there are ten teeth 26 which are distributed in two series of five teeth, the two series being diametrically opposite.

Each tooth 26 extends radially towards the outside and has a sliding surface 32 and a blocking surface 34. The adjacent teeth 26 define notches between them.

The teeth 26 extend from the lower end of the rim 31a (FIG. 3).

As shown in FIG. 2, the cap 8 has a base 36 and two concentric skirts 38, 40 extending longitudinally downwards from the base 36.

The outer skirt 40 encloses the inner skirt 38 and is longer than the skirt 38. An annular space 42 is provided between the skirts 38, 40. The skirt 40 can be elastically deformed by squeezing.

The skirt 38 has an internal thread 44 complementary to the thread 22 and allowing the cap 8 to be screwed onto the neck 14.

The base 36 has an internal feature in the form of a central teat 46 for sealing the duct 16. This teat 46 projects downwards from the base 36.

As shown in FIG. 3, the skirt 40 has two diametrically opposite internal projections 48 provided to cooperate with the lugs 24.

Each projection 48 has a sliding surface 49 and a substantially radial blocking surface 50.

The skirt 40 has external pressing regions 51 for the fingers, which regions are diametrically opposite and offset substantially by 90° about the axis A-A relative to the projections 48.

In a rest configuration of the skirt 40 (FIG. 4), the skirt 40 is substantially circular, and the projections 48 interfere with the lugs 24 of the neck 14 when the cap 8 rotates relative to the neck 14.

The lugs 24 and the projections 48 are oriented in such a way that when the cap 8 rotates relative to the neck 14 in the clockwise screwing direction shown by an arrow V in FIG. 4, the projections 48 and the lugs 24 come into contact via the sliding surfaces 28, 49 thereof. The application of a sufficient torque about the axis A-A on the cap 8 induces, because of the inclination of the sliding surfaces 28, 49, a deformation of the skirt 40 allowing the projections 48 to pass the lugs 24 without preventing the rotation of the cap 8.

If the cap 8 rotates relative to the neck 14 in the counter-clockwise unscrewing direction shown by an arrow D in FIG. 4, the projections 48 and the lugs 24 come into contact with one another via the blocking surfaces 50, 30 thereof and prevent rotation of the cap 8 relative to the neck 14.

As shown in FIG. 5, in a deformed configuration of the skirt 40 brought about by squeezing on the regions 51, the skirt 40 takes on a substantially oval or elliptical shape in such a way that the projections 48 are displaced relative to the resting configuration of the skirt 40. The projections 48 are disengaged from the lugs 24 and it is possible to unscrew the cap 8.

The projections 48 on the elastically deformable skirt 40 and the lugs 24 on the neck 14 form means for the unidirectional blocking of the rotation of the cap 8 relative to the neck 14, which means can prevent the cap 8 from being unscrewed, and can be disengaged by squeezing on the skirt 40 to allow the cap 8 to be unscrewed.

As shown in FIGS. 1, 2 and 6, the ring 10 is formed in one piece with the cap 8 and connected thereto by a brittle region 52 formed by brittle bridges 54 (FIG. 1).

The ring 10 has internal features, comprising teeth 56 (FIG. 6) and ribs 58 (FIG. 2).

The ribs 58 are disposed longitudinally below the teeth 56. In this case, there are three ribs 58 which are regularly distributed about the axis A-A. Each rib 58 extends in a circular arc about the axis A-A and has a domed shape.

As can be seen in FIG. 6, the teeth 56 are complementary to the teeth 26. Each tooth 56 has a sliding surface 60 and a blocking surface 62.

The ring 10 has six teeth 56, distributed in three pairs offset by 120° about the axis A-A.

The teeth 56 and 26 are oriented in such a way that if the ring 10 rotates relative to the neck 14 in the counter-clockwise unscrewing direction shown by the arrow D in FIG. 6, the teeth 56 and 26 come into contact via the blocking surfaces 62, 34 thereof and prevent the rotation of the ring 10 relative to the neck 14.

In the case of rotation in the opposite direction, the teeth 56 and 26 come into contact via the sliding surfaces thereof, and a sufficient torque makes it possible to rotate the ring 10 relative to the neck 14.

The teeth 56 and 26 thus form the means for the unidirectional blocking of the rotation of the ring 10 relative to the neck 14.

The distributions of the teeth 26 and 56 ensure that there are some teeth 26 which are engaged with the teeth 56 when the ring 10 is in position on the neck 14.

The diameter of the ring 10 is such that the ring 10 can be displaced along the neck 14 without radially interfering with the lugs 24.

As shown in FIG. 1, the skirt 40 and the ring 10 have on the adjacent edges 64, 66 thereof complementary notches 68, 70 for blocking the rotation of the cap 8 relative to the ring 10 in the screwing direction.

The skirt 40 and the ring 10 each comprise two diametrically opposite notches 68 and 70 respectively.

The assembly 2 is provided for holding with the end fitting 6, the cap 8 and the ring 10 separated from the vessel 4.

To package the collyrium, the vessel 4 is filled with collyrium, then the end fitting 6 is plugged into the neck 14, and the cap 8, bearing the ring 10, is screwed onto the neck 14.

When the cap 8 is screwed on, the threads 22 and 44 cooperate so as to cause the cap 8 and the ring 10 to descend along the neck 14.

The ring 10 descends along the neck 14 without interfering with the lugs 24. When the ribs 58 meet the teeth 26, it is necessary to apply a greater torque and to push downwards on the cap 8.

The cap 8 pushes the ring 10 downwards and entrains the ring 10 in rotation via the cooperation of the notches 68, 70.

Because of the pushing applied to the ring 10, by virtue of the domed shape of the ribs 58, the teeth 26 cause a slight resilient expansion of the ring 10, which will allow the ribs 58 to pass around the teeth 26.

Because of the cooperation of the notches 68, 70, the bridges 54 are essentially not activated circumferentially when the cap 8 is first screwed on, and the ring 10 is pushed downwards along the neck 14 without breaking the bridges 54.

Screwing on the cap 8 continues until the ribs 58 have passed under the teeth 26 and the teeth 26 are engaged in the notches 56.

When the cap 8 is screwed on, the projections 48 and the lugs 24 come into contact via the sliding surfaces 49 and 28 thereof, causing a deformation of the skirt 40 so as to allow the projections 48 to pass over the lugs 24 without preventing rotation of the cap 8 relative to the neck 14.

When the cap 8 has been screwed on completely, the teat 46 is inserted into the duct 16 and ensures tight closure of the duct 16.

The assembly 2 is then in the assembled pre-use configuration thereof, as shown in FIGS. 1 to 3 and 6.

During the first use and all subsequent uses, if the user only exerts an unscrewing torque on the cap 8 about the axis A-A, the projections 48 and lugs 24 prevent the rotation and unscrewing of the cap 8.

To unscrew the cap 8, the user must exert, simultaneously with the unscrewing torque, a squeezing action on the skirt 40 on the regions 51. As described above, this squeezing action deforms the skirt 40 in such a way that the projections 48 are disengaged from the lugs 24, thus permitting the unscrewing of the cap 8.

The squeezing must be performed at least in an initial phase of the unscrewing of the cap 8, until the projections 48 are longitudinally offset relative to the lugs 24.

When the assembly 2 is first opened, the user squeezes the skirt 40 and applies a torque to unscrew the cap 8. The threads 22 and 44 cooperate so as to cause upward displacement of the cap along the neck 14.

The cap 8 is connected to the ring 10 by the bridges 54 in such a way that the cap 8 entrains the ring 10. The teeth 26 and 56 prevent the ring 10 from rotating relative to the neck 14. As the unscrewing of the cap 8 continues, the bridges 54 are stretched, and this quickly causes them to break.

The cap 8 is then separated from the ring 10, and it is possible to continue the unscrewing of the cap 8 freely until said cap is completely disengaged from the neck 14.

The ribs 58 hold the ring 10 on the neck 14 when the cap 8 is removed, to prevent the ring 10 from falling, in particular when the vessel 4 is turned upside-down to dispense drops into the eye.

Between two uses, the cap 8 is closed again simply by applying a screwing torque, because this direction of rotation is permitted by the projections 48 and the lugs 24.

The screw pitch of the threads 22 and 44 and the height of the projections 48 and the lugs 24 are preferably selected in such a way that when the cap 8 is unscrewed, each projection 48 passes opposite and at the height of at least two lugs 24 so as to limit still further the risk of a child opening the vessel 4, if the child should, by chance, manage to unscrew the cap partially so as to pass one lug 24.

The height of the teat 46 is preferably selected in such a way that the teat 46 seals the duct 16 tightly at least over the part of the axial path of the cap during which the safety means are operational, i.e. until the projections 48 have passed over the lugs 24.

In this way, the vessel 4 remains closed until the safety means are inoperative, and this reduces the risk of liquid being expelled before the cap 8 has been completely and intentionally unscrewed, and ensures the tightness and sterility of the vessel 4.

To dispense the collyrium, the user grasps the open vessel 4, generally between the thumb and the index finger of one hand, turns the vessel 4 upside-down, and squeezes the vessel between his fingers to expel a specific number of drops.

The vessel 4, the end fitting 6 and the cap 8 must meet certain requirements in connection with the holding of collyria, to the child safety function, and to the dispensing of calibrated drops of liquid by squeezing the vessel 4 between the fingers of one hand.

The vessel 4 and the end fitting 6 must make squeezing between the fingers possible. The force must be such that it can be applied by an individual, in particular an elderly person, by squeezing, and must be approximately 35 N to 40 N.

To achieve this, the vessel must be sufficiently flexible. However, the vessel 4 has low dimensions which reduce its flexibility. Specifically, because of their dosages, collyria are packaged in low-capacity vessels 4. Conventional dosing involves applying two drops of collyrium, once or twice a day, for one or two weeks. The size of a drop of collyrium is approximately 40 µl.

Thus, the vessel 4 has a capacity of less than 30 ml, preferably less than 20 ml. For example, it is possible to provide a range of vessels with capacities of 5 ml, 10 ml and 15 ml.

The resulting low dimensions of the vessel 4 reduce its flexibility. The body 14 of the vessel 4 typically has a diameter of approximately 25 mm and a height of approximately 15 to 50 mm, according to the capacity thereof.

The end fitting 6 has particular dimensions making its manufacture compatible with regulating the calibration of the drops. The dimensions of the neck 14 must correspond to those of the end fitting 6 to ensure tight closure of the neck 14 by the end fitting 6, at the periphery of the end fitting 6. It is also preferable to be able to use an already existing end fitting having predetermined dimensions.

Furthermore, to provide the child safety function, the neck 14, and in particular the lugs 24, and the cap 8, and in particular the skirt 40, must have a particular rigidity so that the application of a high unscrewing torque will not allow the lugs 24 and the projections 48 to escape the rotational blocking.

For these reasons, the vessel 4 is made in one piece, from a material or a mixture of materials with a Young's modulus E1 lower than the Young's modulus E2 of the material or mixture of materials forming the cap 8, which is also in one piece.

The following materials are compatible with medical use and can be used to produce the vessel 4 and the cap 8: low-density polyethylene (LDPE), medium-density polyethylene (MDPE), high-density polyethylene (HDPE), polypropylene and polyethylene terephthalate (PET).

LDPE has a density between 0.920 and 0.930. HDPE has a density between 0.940 and 0.960. MDPE has a density between 0.930 and 0.940.

LDPE and HDPE are particularly advantageous as regards the low production cost thereof. Furthermore, LDPE, MDPE and HDPE can be mixed easily and can be used in injection blow molding manufacturing processes which are advantageous for producing vessels in these materials.

LDPE has a lower Young's modulus than MDPE, which in turn has a lower Young's modulus than HDPE. A mixture will have an intermediate Young's modulus as a function of the relative LDPE, MDPE and HDPE contents of the mixture.

It is thus advantageous to produce the vessel 4 from LDPE or from a mixture of LDPE with MDPE and/or HDPE, and the cap 8 from a mixture of LDPE with MDPE and/or HDPE, from MDPE or from a mixture of MDPE and HDPE, or from HDPE.

Preferably, to obtain sufficient rigidity for the cap 8, the mixture forming the cap 8 is at least 20% by mass HDPE.

In a particular embodiment, the vessel 4 is made purely from LDPE, and the cap 8 is made from a mixture of LDPE and HDPE.

The neck 14 has a reduced diameter by comparison with the skirt 40, in such a way that the lugs 24 have a substantial length L. Furthermore, each lug 24 narrows towards the outer end thereof because of the provision of a sliding surface 28.

To provide sufficient flexural rigidity for each lug 24, in particular at the outer end thereof, each lug 24 has a substantially planar transition surface 31 extending between the sliding surface 28 thereof and the blocking surface 30 thereof.

Thus, each lug 24 has, over the entire length L thereof (FIG. 4), a minimum thickness e (FIG. 4), preferably greater than 0.5 mm Furthermore, the sliding surface 28 is in the form of a chamfer between a face of the lug 24 opposite the blocking surface 30 and the transition surface 31. A sliding surface 28 of this type ensures sufficient sliding, while limiting the reduction of the flexural rigidity of the outer end portion of the lug 24.

Furthermore, because each lug 24 presses on the rim 31a, each lug 24 is rigidified.

The assembly 2, according to the invention, makes it possible to prevent the cap 8 from being opened simply by applying an unscrewing torque to the cap 8. This reduces the risk of a child succeeding in opening the assembly 2.

The assembly 2 also has a first-use indicator, which ensures the safety of use of the assembly 2.

The two independent skirts 38 and 40 allow a simple, low-cost manufacture of the cap 8 while integrating various functions into said cap (screwing, safety, first-use indicator).

The invention is equally applicable to assemblies for holding and dispensing other medical liquids provided for drop-by-drop dispensing, such as solutions for the nose or the ears.

The invention claimed is:

1. An assembly for holding and dispensing a medical liquid, comprising:
   a vessel (4) for containing the liquid, the vessel (4) having a neck (14);
   a dispensing dropper end fitting (6) disposed at an end of the neck (14), the end fitting (6) and the vessel (4) configured to allow the liquid to be dispensed drop by drop by squeezing the vessel (4) between fingers of one hand;
   a cap (8) for closing the vessel (4), configured to be screwed onto the neck (14); and
   a first-opening indicator comprised of a tamper-evident band (10) connected to the cap (8) by a brittle region (52) configured to break when the cap (8) is first opened,
   wherein the vessel is suitable to contain an ophthalmic medical liquid of collyrium type,
   wherein the cap (8) and the neck (14) have a safety device configured to prevent the cap (8) from being unscrewed from an application of an unscrewing torque alone, and to allow the cap (8) to be unscrewed when an additional action is applied together with the unscrewing torque for unscrewing the cap (8), and
   wherein the vessel (4) and the cap (8) are each made from low-density polyethylene (LDPE) and high-density polyethylene (HDPE), the cap (8) having a greater proportion by mass of high-density polyethylene (HDPE) to low-density polyethylene (LDPE) than that of the vessel (4).

2. The assembly according to claim 1, wherein the vessel (4) has a Young's modulus (E1) less than a Young's modulus (E2) of the cap (8).

3. The assembly according to claim 1, wherein the vessel (4) has a capacity of less than 30 ml.

4. The assembly according to claim 1, wherein the safety device makes it possible to unscrew the cap (8) if the cap (8) is squeezed during the unscrewing.

5. The assembly according to claim 1,
   wherein the safety device has means (48, 24) for unidirectional blocking of a rotation of the cap (8) relative to the neck (14), and
   wherein it is possible to disengage the unidirectional blocking means by squeezing the cap (8).

6. The assembly according to claim 1, wherein the cap (8) has an element configured to close the end fitting (6) tightly and sealing the end fitting (6) at least over a part of the path of the cap (8) during which the safety device operates to ensure tightness and sterility of the interior of the vessel (4).

7. The assembly according to claim 1, wherein the vessel (4) has a capacity of less than 20 ml.

8. An assembly for holding and dispensing a medical liquid, comprising:
   a vessel (4) for containing the liquid, the vessel (4) having a neck (14);
   a dispensing dropper end fitting (6) disposed at an end of the neck (14), the end fitting (6) and the vessel (4) configured to allow the liquid to be dispensed drop by drop by squeezing the vessel (4) between fingers of one hand;
   a cap (8) for closing the vessel (4), configured to be screwed onto the neck (14); and
   a first-opening indicator comprised of a tamper-evident band (10) connected to the cap (8) by a brittle region (52) configured to break when the cap (8) is first opened,
   wherein the vessel is suitable to contain an ophthalmic medical liquid of collyrium type, wherein the cap (8) and the neck (14) have a safety device configured to prevent the cap (8) from being unscrewed from an application of an unscrewing torque alone, and to allow the cap (8) to be unscrewed when an additional action is applied together with the unscrewing torque for unscrewing the cap (8), wherein the vessel (4) consists purely of low-density polyethylene (LDPE), and wherein the cap (8) comprises at least 20% by mass of high-density polyethylene (HDPE), the remainder consisting of low-density polyethylene (LDPE).

9. The assembly according to claim 8, wherein the vessel (4) has a Young's modulus (E1) less than a Young's modulus (E2) of the cap (8).

10. The assembly according to claim 8, wherein the vessel (4) has a capacity of less than 30 ml.

11. The assembly according to claim 8, wherein the safety device makes it possible to unscrew the cap (8) if the cap (8) is squeezed during the unscrewing.

12. The assembly according to claim 8,
wherein the safety device has means (48, 24) for unidirectional blocking of a rotation of the cap (8) relative to the neck (14), and
wherein it is possible to disengage the unidirectional blocking means by squeezing the cap (8).

13. The assembly according to claim 8, wherein the cap (8) has an element configured to close the end fitting (6) tightly and sealing the end fitting (6) at least over a part of the path of the cap (8) during which the safety device operates to ensure tightness and sterility of the interior of the vessel (4).

14. The assembly according to claim 8, wherein the vessel (4) has a capacity of less than 20 ml.

15. An assembly for holding and dispensing a medical liquid, comprising:
a vessel (4) for containing the liquid, the vessel (4) having a neck (14);
dispensing dropper end fitting (6) disposed at an end of the neck (14), the end fitting (6) and the vessel (4) configured to allow the liquid to be dispensed drop by drop by squeezing the vessel (4) between fingers of one hand;
a cap (8) for closing the vessel (4), configured to be screwed onto the neck (14); and
a first-opening indicator comprised of a tamper-evident band (10) connected to the cap (8) by a brittle region (52) configured to break when the cap (8) is first opened,
wherein the cap (8) and the neck (14) have a safety device configured to prevent the cap (8) from being unscrewed from an application of an unscrewing torque alone, and to allow the cap (8) to be unscrewed when an additional action is applied together with the unscrewing torque for unscrewing the cap (8),
wherein the vessel is suitable to contain an ophthalmic medical liquid of collyrium type,
wherein the safety device has means (48, 24) for unidirectional blocking of a rotation of the cap (8) relative to the neck (14),
wherein the unidirectional blocking means is disengageable by squeezing the cap (8), and
wherein the cap (8) has a first external skirt (40), the first external skirt (40) being coaxial with and enclosing a second skirt (38) that bears a thread (44) for screwing the cap (8) onto the neck (14), the blocking means having at least one internal feature (48) on the first external skirt (40) and at least one external feature (24) on the neck (14), said at least one internal feature (48) and said at least one external feature (24) being complementary to each other and disengageable from one another by squeezing the first external skirt (40) in two pressing regions (51) which are angularly offset relative to each internal feature (48).

16. The assembly according to claim 15, wherein the blocking means have two diametrically opposite internal features (48) disposed on the first external skirt (40) and angularly offset by 90° relative to the pressing regions (51), the neck (14) comprising two diametrically opposite external features (24).

17. The assembly according to claim 16, wherein each external feature of the neck (14) is formed by a lug (24) projecting radially towards an outside of the neck (14),
the lug (24) having a radial blocking surface (30), a sliding surface (28) inclined as a whole relative to the blocking surface (30), and a transition surface (31) extending between the blocking surface (30) and the sliding surface (28), the transition surface (31) being substantially perpendicular to the blocking surface (30).

18. The assembly according to claim 15, wherein each external feature of the neck (14) is formed by a lug (24) projecting radially towards an outside of the neck (14),
the lug (24) having a radial blocking surface (30), a sliding surface (28) inclined as a whole relative to the blocking surface (30), and a transition surface (31) extending between the blocking surface (30) and the sliding surface (28), the transition surface (31) being substantially perpendicular to the blocking surface (30).

19. The assembly according to claim 15, wherein the neck (14) has an annular reinforcing rim (31a) extending so as to project towards the outside of the neck (14) and passing through the external features (24) so as to rigidify them.

20. The assembly according to claim 15, wherein the vessel (4) is made of a material or mixture of materials having a Young's modulus (E1) less than a Young's modulus (E2) of a material or mixture of materials of which the cap (8) is made.

21. The assembly according to claim 15, wherein the vessel (4) and the cap (8) are each made from a material or mixture of materials selected from the materials consisting of: low-density polyethylene (LDPE), medium-density polyethylene (MDPE), high-density polyethylene (HDPE), polypropylene, and
polyethylene terephthalate (PET).

22. The assembly according to claim 15, wherein the vessel (4) has a capacity of less than 30 ml.

23. The assembly according to claim 15, wherein the cap (8) has an element configured to close the end fitting (6) tightly and sealing the end fitting (6) at least over a part of the path of the cap (8) during which the safety device operates to ensure tightness and sterility of the interior of the vessel (4).

24. The assembly according to claim 15, wherein the vessel (4) has a capacity of less than 20 ml.

* * * * *

UNITED STATES PATENT AND TRADEMARK OFFICE
CERTIFICATE OF CORRECTION

PATENT NO. : 8,444,610 B2  Page 1 of 1
APPLICATION NO. : 12/522793
DATED : May 21, 2013
INVENTOR(S) : Guillaume Grevin It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 849 days.

Signed and Sealed this

Eighth Day of September, 2015

Michelle K. Lee
*Director of the United States Patent and Trademark Office*